United States Patent [19]
Sharpless et al.

[11] Patent Number: 6,057,473
[45] Date of Patent: *May 2, 2000

[54] SYNTHESIS OF ARYL SERINES

[75] Inventors: K. Barry Sharpless, La Jolla, Calif.; Beata Tao, Cambridge, Mass.; Gunther Schlingloff, Riehen, Switzerland

[73] Assignee: The Scripps Research Institute, Calif.

[ * ] Notice: This patent is subject to a terminal disclaimer.

[21] Appl. No.: 09/050,222

[22] Filed: Mar. 26, 1998

Related U.S. Application Data

[63] Continuation-in-part of application No. 08/651,104, May 21, 1996, Pat. No. 5,767,304.

[51] Int. Cl.[7] .................................................. C07C 229/28
[52] U.S. Cl. ............................... 560/38; 540/27; 540/29; 540/39; 540/115; 540/160
[58] Field of Search ................................ 560/27, 29, 115, 560/160, 38, 39

[56] References Cited

U.S. PATENT DOCUMENTS 5,767,304   6/1998   Sharpless et al. ........................ 560/27

*Primary Examiner*—Gary Geist
*Assistant Examiner*—Brian J. Davis
*Attorney, Agent, or Firm*—Donald G. Lewis

[57] ABSTRACT

Anthraquinone chiral ligands (AQN) are used in asymmetric aminohydroxylation addition reactions of cinnamate based olefins for synthesizing aryl serines. The anthraquinones impart a reverse regioselectivity as compared to the commonly employed phalazine chiral ligands (PHAL). Carbamates are employed as the oxidant nitrogen source. The yields and enantiomeric efficiencies are Excellent. β-Hydroxyamines are obtained by deprotecting the corresponding β-hydroxycarbamate.

4 Claims, 15 Drawing Sheets

| Entry | X = | Regioselectivity[a] (1 : 2) | Yield of 1[b] | (DHQ)$_2$AQN % ee[c] | (DHQD)$_2$AQN % ee[c] |
|---|---|---|---|---|---|
| 1 | H | 80:20 | 62% | 95 | 92 |
| 2 | 4-fluoro | 80:20 | 68% | 91 | 92 |
| 3 | 4-chloro | 80:20 | 54% | 91 | 92 |
| 4 | 4-bromo | 80:20 | 52% | 89 | 89 |
| 5 | 4-methyl | 80:20 | 52% | 93 | 96 |
| 6 | 4-methoxy | 75:25 | 65% | 94 | 93 |
| 7 | 2,6-dimethoxy | 75:25 | 51% | 91 | 91 |
| 8 | 4-benzyloxy | 66:34 | 40% | 87 | 87 |

FIG. 1B

| Entry | Substrate | Product | %ee (DHQ)$_2$PHAL | %ee (DHQD)$_2$PHAL | Yield (%) | Time (h) |
|---|---|---|---|---|---|---|
| 1 | Ph～CO$_2$CH$_3$ | ZNH/Ph—CO$_2$CH$_3$/OH 1 | 94 | 97 | 55 | 1.5 |
| 2 | Me-aryl-CO$_2$CH$_3$ | Me-ZNH-aryl-CO$_2$CH$_3$/MeOH 2 | 94 | 82 | 61 | 2 |
| 3[a] | H$_3$CO$_2$C～CO$_2$CH$_3$ | ZNH/H$_3$CO$_2$C—CO$_2$CH$_3$/OH 3 | 84 | 87 | 55 | 24 |
| 4 | cyclohexene | ZNH/OH 4 | 63 | 56 | 51 | 2 |
| 5[b] | Ph～Ph | ZNH/Ph—Ph/OH 5 | 91 | 88 | 92 | 3 |
| 6[b] | naphthyl-vinyl | ZNH/naphthyl/OH 6 | 99 | 99 | 70 | 3 | a. CH$_3$CN/H$_2$O was used as the solvent; b. the reaction was run at 0 °C.
c. Z = (EtO$_2$C)

FIG. 2

43 %ee, 53 % yield

85 %ee, 75 % yield (99% ee for the other enantiomer from (DHQD)$_2$PHAL ligand AA)

98 %ee, ~60 % yield (98% ee for the other enantiomer from (DHQD)$_2$PHAL ligand AA)

97 %ee, ~80 % yield

93 %ee, ~50 % yield (77% ee for the other enantiomer from (DHQ)$_2$PHAL ligand AA)

Dihedral angles:

C1-Os-N-C2 = -0.7°
Os-N-C2-C1 = 0.9°
N-C2-C1-Os = -0.8°
C2-C1-Os-N = 0.7°

C1-Os-N-C2 = -2.1°
Os-N-C2-C1 = 2.7°
N-C2-C1-Os = -2.5°
C2-C1-Os-N = 2.0°

Bond angles:

C1-Os-N = 63.6°
Os-N-C2 = 104.4°
N-C2-C1 = 96.5°
C2-C1-Os = 95.4°
Os-N-S = 130.5°
S-N-C2 = 116.5°

C1-Os-N = 64.1°
Os-N-C2 = 103.5°
N-C2-C1 = 97.8°
C2-C1-Os = 94.5°
Os-N-S = 136.4°
S-N-C2 = 120.0°

N-Methylsulfonyl-
osmaazetidine

N-Methoxycarbonyl-
osmaazetidine (Becke3LYP, LanL2DZ basis set)

SYNTHESIS OF ARYL SERINES

CROSS-REFERENCE TO RELATED APPLICATION

The instant application is filed as a continuation-in-part of copending U.S. application Ser. No. 08/651,104, filed May 21, 1996.

GOVERNMENT RIGHTS

This invention was made with government support under Grant No. GM 28384 awarded by the National Institutes of Health and Grant No. CHE-9531152 awarded by the National Science Foundation. The U.S. government has certain rights in the invention.

FIELD OF INVENTION

The invention relates to the synthesis of aryl serines. More particularly, the invention relates to the regio-selective and enantio-selective conversion of olefins to β-hydroxyamines and β-hydroxycarbamates.

BACKGROUND

Over the past 20 years, separate and distinct synthetic methodologies have been developed by Sharpless et al. for the vicinal hydroxyamination of olefins. There are three major groups of oxyamination procedures which produce aminoalcohols (Sharpless et al. *J. Am. Chem. Soc.* 1975, 97, 2305; Sharpless et al. *J. Org. Chem.* 1978, 43, 2628; Sharpless et al. *J. Org. Chem.* 1980, 45, 2257), hydroxysulfonamides (Sharpless et al. *J. Org. Chem.* 1976, 41, 177; Sharpless et al. *J. Org. Chem.* 1978, 43, 2544; Sharpless et al. *J. Org. Chem.* 1979, 44, 1953; Sharpless et al. *Org. Syn.* 1980, 61, 85) or hydroxycarbamates (Sharpless et al. *J. Am. Chem. Soc.* 1978, 100, 3596; Sharpless et al. *J. Org. Chem.* 1980, 45, 2710; Sharpless et al. U.S. Pat. Nos. 4,871,855; 4,965,364; 5,126,494; EP 0 395 729). Each oxyamination procedure has unique reaction conditions and includes variations in solvents, auxiliary salts, nucleophiles, temperature, stoichiometric v. catalytic amounts of osmium species and stoichiometric v. catalytic amounts of ligand. Each procedure is highly dependant on the nature of the substrate and possesses unique properties which afford different yields, chemoselectivities, stereoselectivities, regioselectivities and enantioselectivitive outcomes.

What is needed is a method for regioselectively and enantiomerically catalyzing the asymmetric aminohydroxylation of cinnamate based olefinic substrates using carbamate oxidants for producing aryl serines.

SUMMARY OF INVENTION

One aspect of the invention is directed to a method for synthesizing an aryl serine. In the first step of the synthesis, a cinnamate based olefinic substrate is converted to an asymmetric β-hydroxycarbamate product by asymmetric addition of an carbamoyl radical and a hydroxyl radical to the olefinic substrate. The method employs a reaction solution which includes a carbamate as a source of the carbamoyl radical, osmium as a catalyst, an anthraquinone based chiral ligand for regioselectively and enantiomerically directing said asymmetric addition, and a solvent having an organic component. Preferred anthraquinone based chiral ligand include (dihyrodquininyl)$_2$-AQN and (dihyrodquindinyl)$_2$-AQN. Preferred organic components of the solvent include acetonitrile, tert-butanol, ethanol, and n-propanol. In a preferred mode, the aqueous and organic components of the solvent are each approximately 50% on a volume basis. The cinnamate based olefinic substrate and carbamate is present and soluble in stoichiometric amounts within the solvent. The osmium is present and soluble in catalytic amounts within the solvent. The anthroquinone (AQN) based chiral ligand is present and soluble within the solvent. The asymmetric β-hydroxycarbamate product is then optionally cleaved for producing the aryl serine.

Another aspect of the invention is directed to the controlled reversed regioselectivity of the asymmetric aminohydroxylation (AA) reaction (from that of the regioselectivity found with PHAL ligands) on cinnamate based olefins using AQN ligands. In particular, the reversed regioselectivity of the AA reaction is carried out in a reaction solution which includes the cinnamate based olefinic substrate, an osmium catalyst, an AQN chiral ligand for enantiomerically and regioselectively directing the asymmetric addition, a carbamate, and a solvent or co-solvent. The carbamate serves as a source for the carbamoyl radical. The olefinic substrate and carbamate are present and soluble within the solvent or cosolvent in stoichiometric amounts. The osmium is present within the solvent or co-solvent in catalytic amounts.

DESCRIPTION OF FIGURES

FIG. 2 shows the regular AA using the PHAL-ligands olefin substrate—the AQN demonstrates reversed regioselectivity on these olefins to the hydroxy-carbamate product, % ee (enantioselectivity) with the (DHQ)$_2$PHAL (DHQ= hydroquinine; PHAL=phthalazine) or (DHQD)$_2$PHAL (DHQD=hydroquinidine) ligands, % yields and time (h).

DETAILED DESCRIPTION

I. Reversal of Regioselection in the Asymmetric Aminohydroxylation of Cinnamates Use of cinchona ligands with an anthraquinone (AQN) core, in place of the usual phthalazine (PHAL) core, in the asymmetric aminohydroxylation of cinnamates causes dramatic reversal of the regioselection, so that phenyl serines are obtained in high enantiomeric excess. Hence, the regioselectivity outcome (i.e. isoserine vs. serine) is controlled by the ligand and not the substrate.

The asymmetric aminohydroxylation (AA) is a one-step stereospecific conversion of olefins to protected—aminoalcohols using catalytic amounts of an osmium source and chiral ligands based on cinchona alkaloids. Three different types of N-haloamine salts were found to deliver the nitrogen heteroatom while also serving as the ultimate oxidant. The fact that sulfonamides, amides, and carbamates can be used, simplifies catalysis optimization and leaves a certain flexibility when planning a reaction sequence with the AA products. The most significant method for a synthetic chemist surely is the carbamate modification, since numerous deprotection methods for reductive (CBz), acidic (t-BOC), and nucleophilic (Teoc) removal are known.

The aminohydroxylation works particularly well for E-3-substituted acrylate esters [E—RCH=CHCOOR', R=aryl or alkyl]. In recent studies on the N-bromoacetamide-based AA, it was noted that the anthraquinone ligands (DHQ)$_2$AQN and (DHQD)$_2$AQN$_6$ imposed a regioselectivity pattern different from that seen with their more commonly used PHAL-analogs (Bruncko et al. *Angew. Chem. Int. Ed. Engl.* 1997, 36, 1483–1486). For example, in the transformation of styrenes, the amide-based AA's preference for placing the nitrogen on the terminal nonbenzylic carbon is accentuated using the AQN-ligands. In pursuing this phenomenon and using N-chloro-N-sodio carbamates for the AA of cinnamates, it is reported herein that the serine regioisomers B (FIG. 1) are strongly favored using the AQN-ligands (c.f. PHAL-ligands which give the isoserine isomers A1; Li et al. *Angew. Chem. Int. Ed. Engl.* 1996, 35, 2813–2817.

Figure 1A:
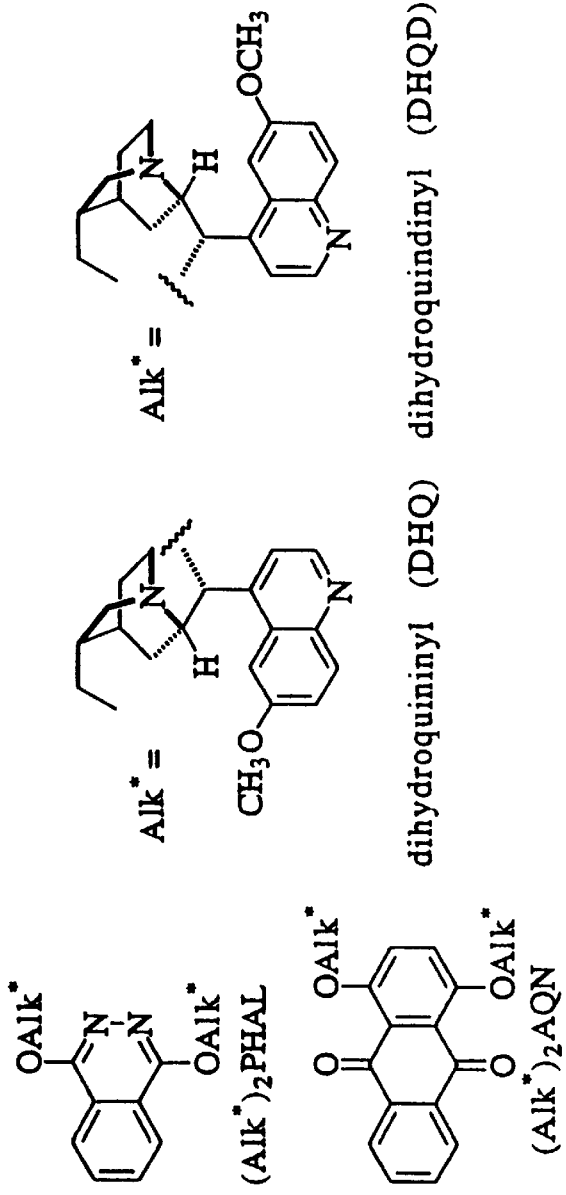
FIG. 1 illustrates: A) the AA of cinnamates using N-chloro-N-sodio carbamates and AQN ligands wherein the serine regioisomers B (REVERSED REGIOISOMER FROM PHAL-LIGANDS) are strongly favored with the AQN-ligands. [Alk*=dihydroquininyl (DHQ) or -quinidinyl (DHQD)]; B) tabulation of results of reverse regioselection for various asymmetric aminohydroxylation of methyl cinnamates using CBzNClNa and AQN ligands with the following notes: a) See protocals for standard reaction conditions using AQN ligands in lieu of PHAL-ligands; CBz= Benzyloxycarbonyl. b) Determined by $^1$H-NMR; c) Products obtained using (DHQ)$_2$AQN. Ee's (enantiomeric excess) were determined on chiral stationary HPLC columns (CHIRALCEL (™) OD-H or CHIRALPAK (™) AS, DAICEL (™). d) Products obtained using (DHQD)$_2$AQN. e) Not determined. f) HPLC analysis of the minor regioisomer [(2R,3S)-A] revealed an ee of 91%. g) Regioisomers were inseparable by chromatography. h) Ethyl cinnamate was used in place of methyl cinnamate.
Figure 1A:
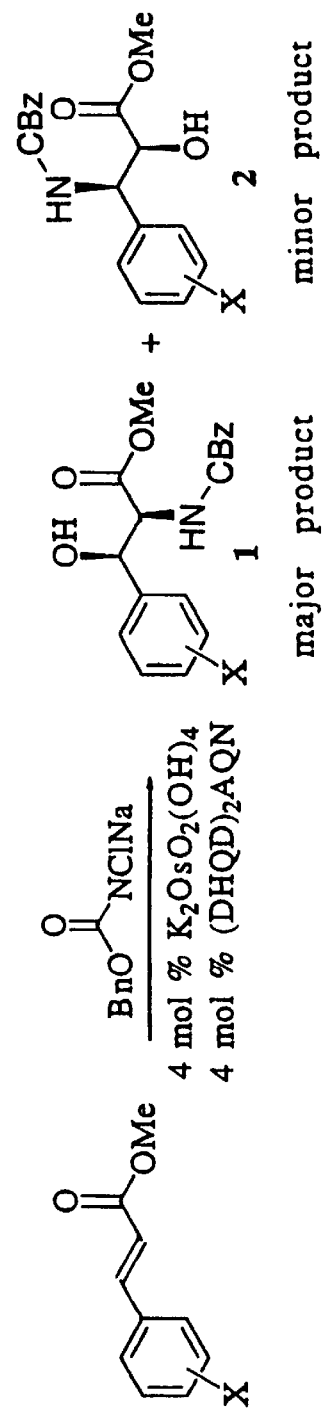
Figure 3:
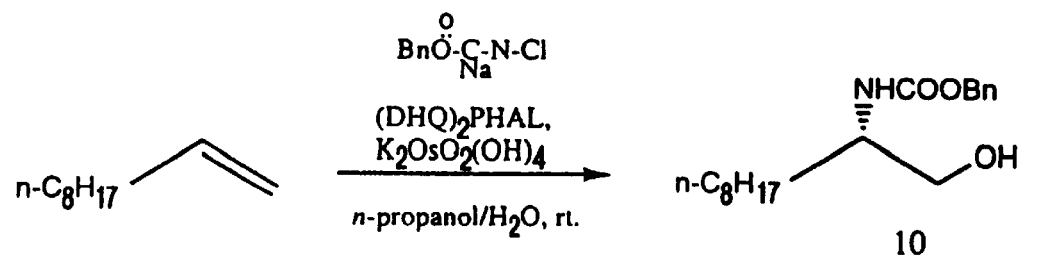
FIG. 3 illustrates conversion of a variety of olefins showing the regular AA using the PHAL-ligands with noted conditions, yields and % ee.
Figure 3:
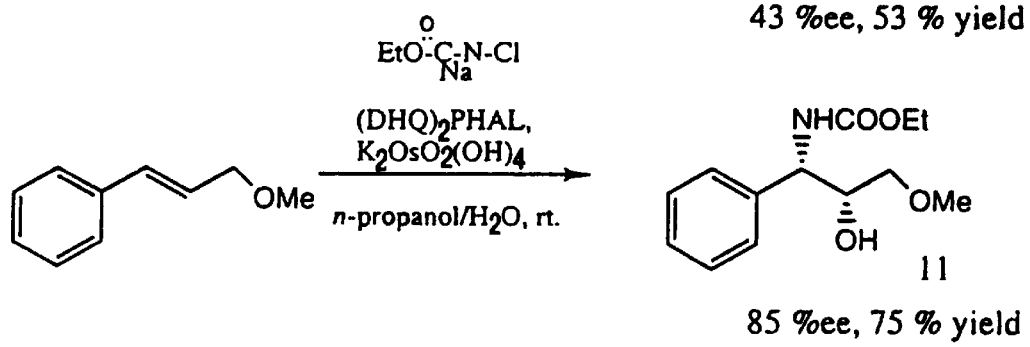
Figure 3:
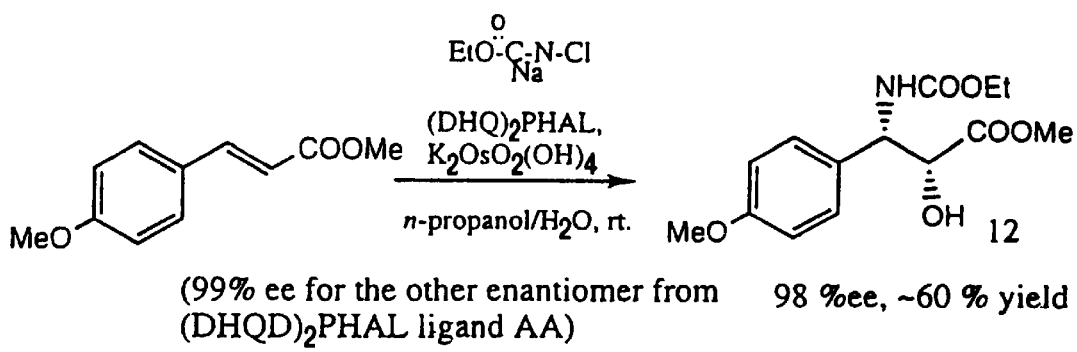
Figure 3:
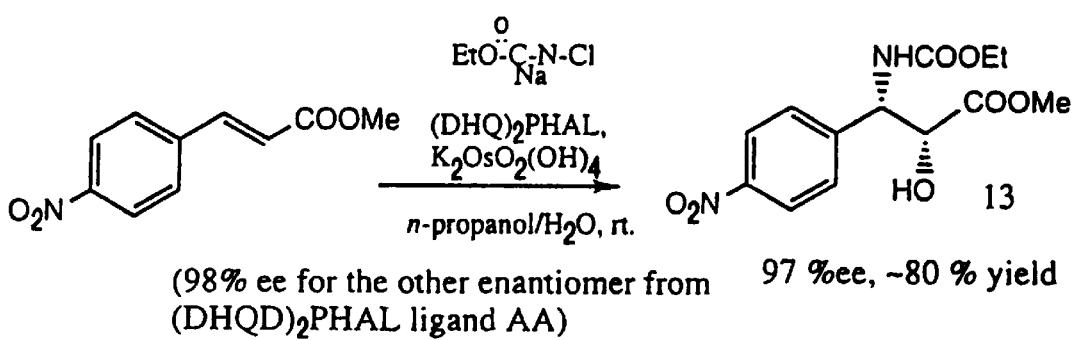
Figure 3:
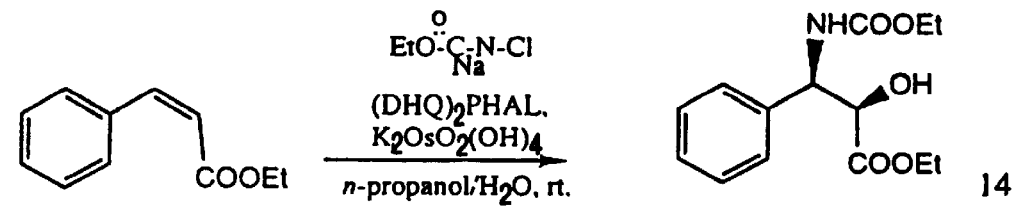
Figure 4:
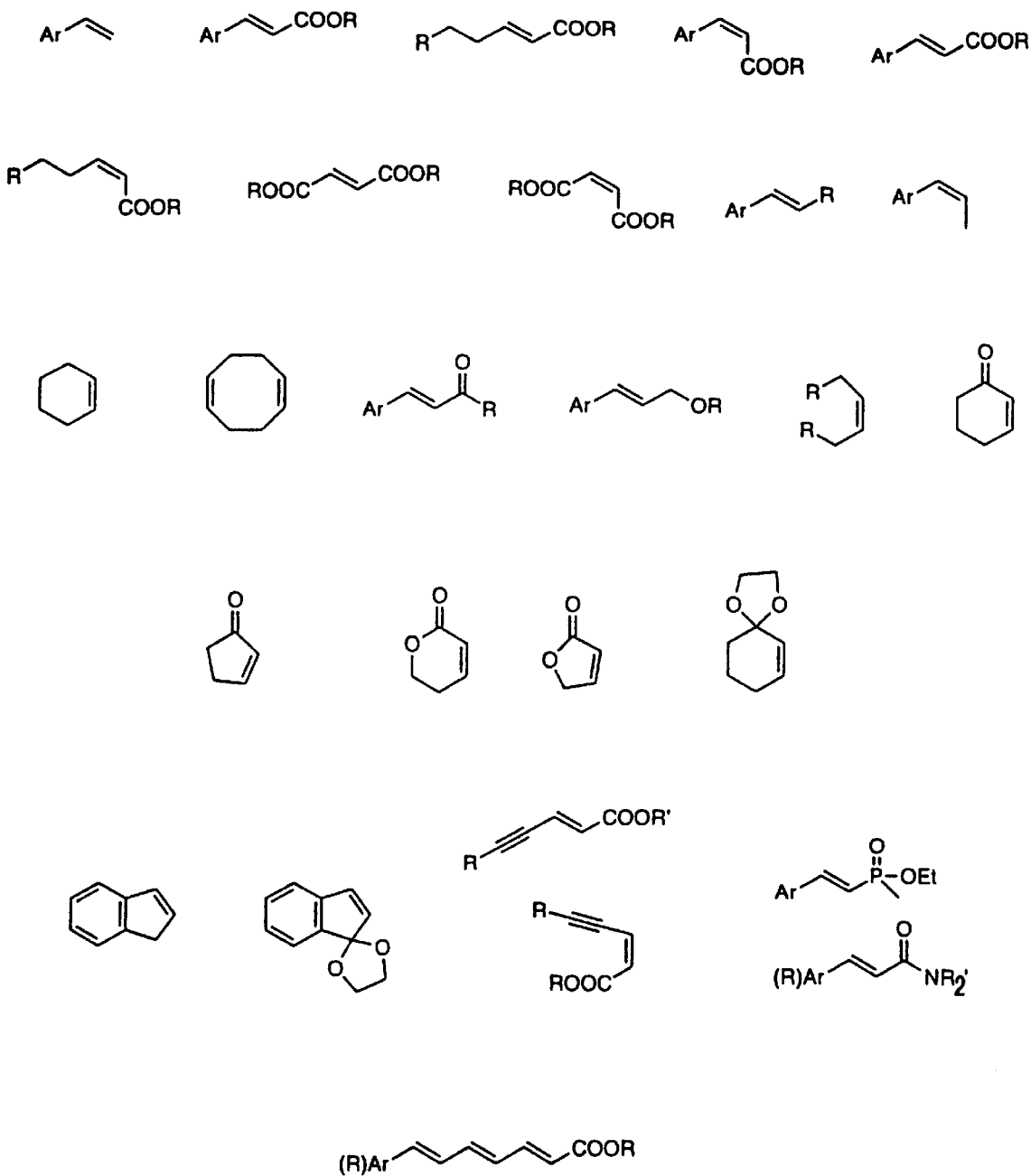
FIG. 4 shows a series of preferred substrate olefins where R=hydrogen, aromatic, alkyl, heterocycles, hydroxyl substituents, esters, ethers, as appropriate for substrate.
Figure 5:
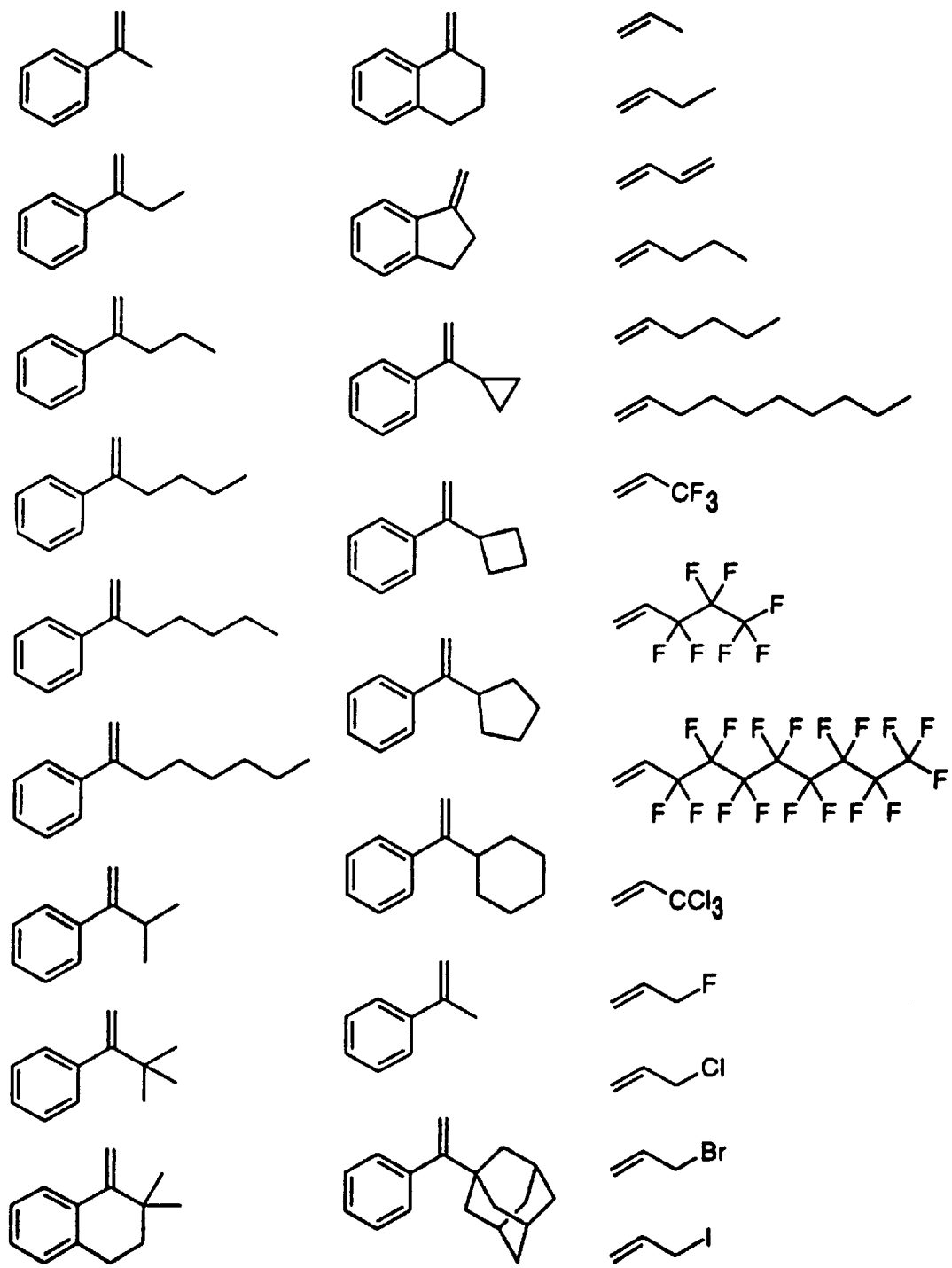
FIG. 5 illustrates a series of compatible olefins for aminohydroxylation including some 1,1 disubstituted and monosubstituted olefins with various functionalities.
Figure 6:
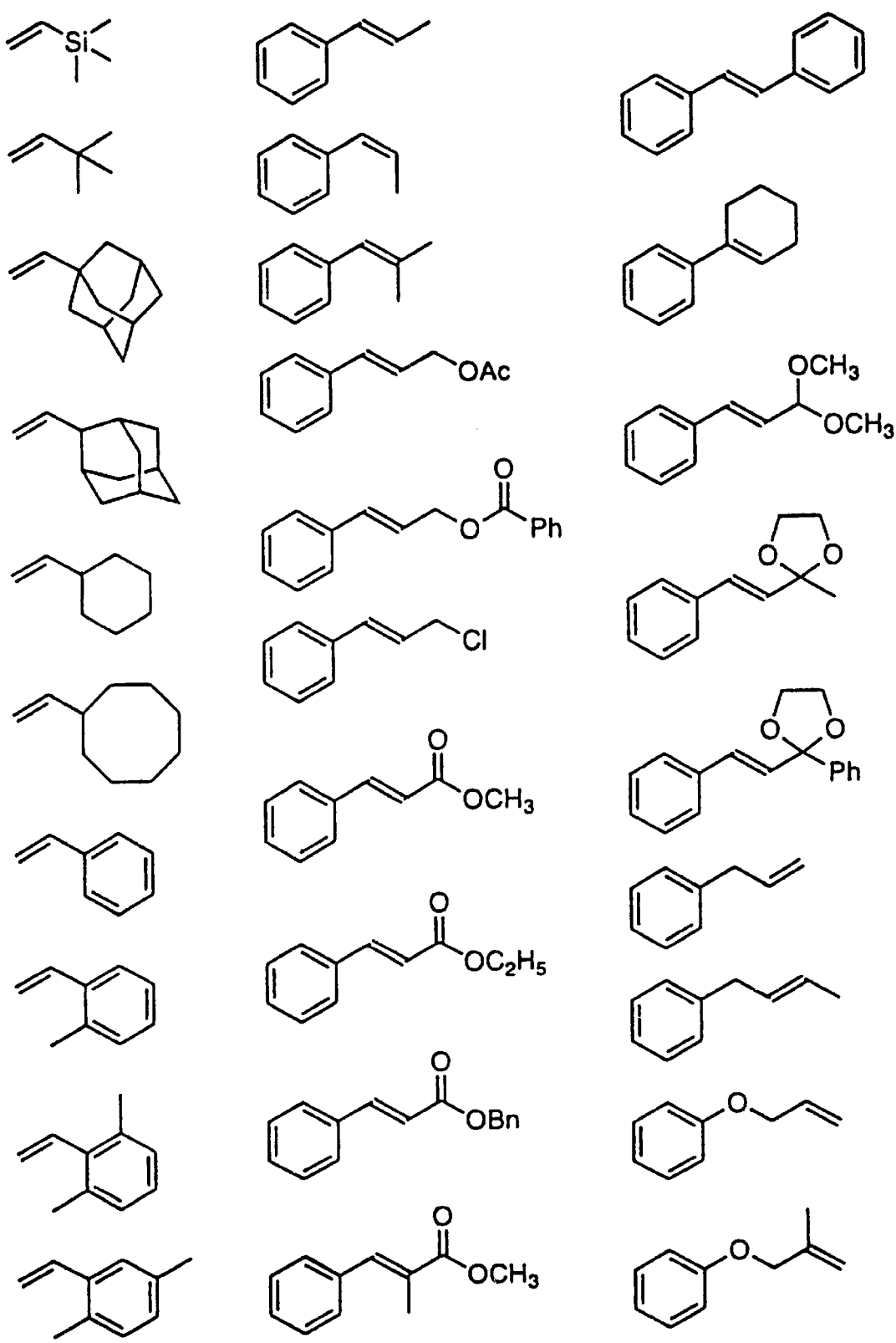
FIG. 6 illustrates a series of compatible olefins for aminohydroxylation including some monosubstituted and disubstituted olefins (cis and trans) with various functionalities.
Figure 7:
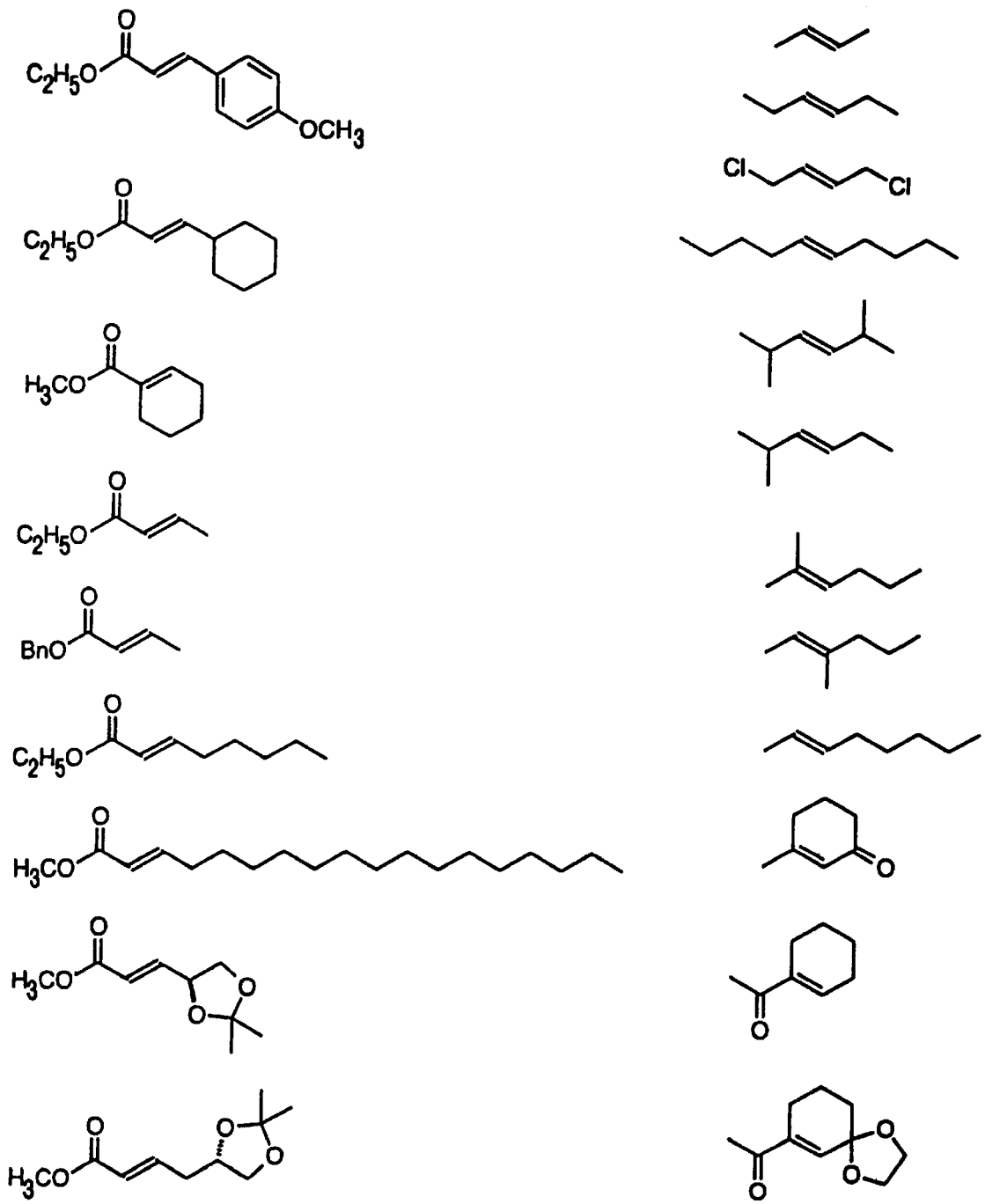
FIG. 7 illustrates a series of disubstituted olefins for asymmetric aminohydroxylation with various functionalities.
Figure 8:
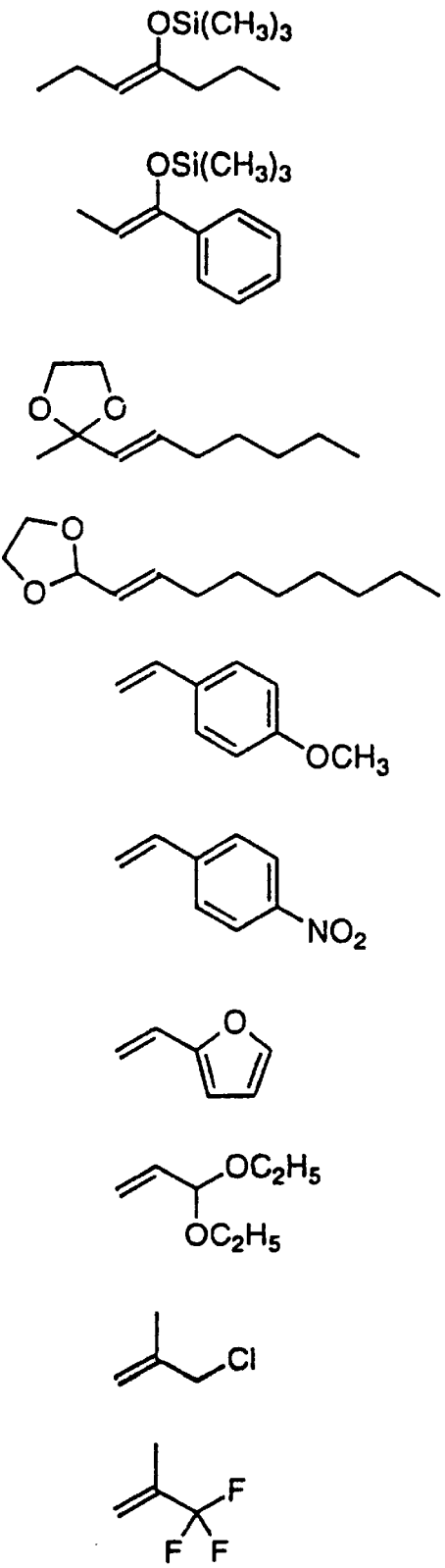
FIG. 8 illustrates a series of monosubstituted and disubstituted olefins for aminohydroxylation with various functionalities.
Figure 9:
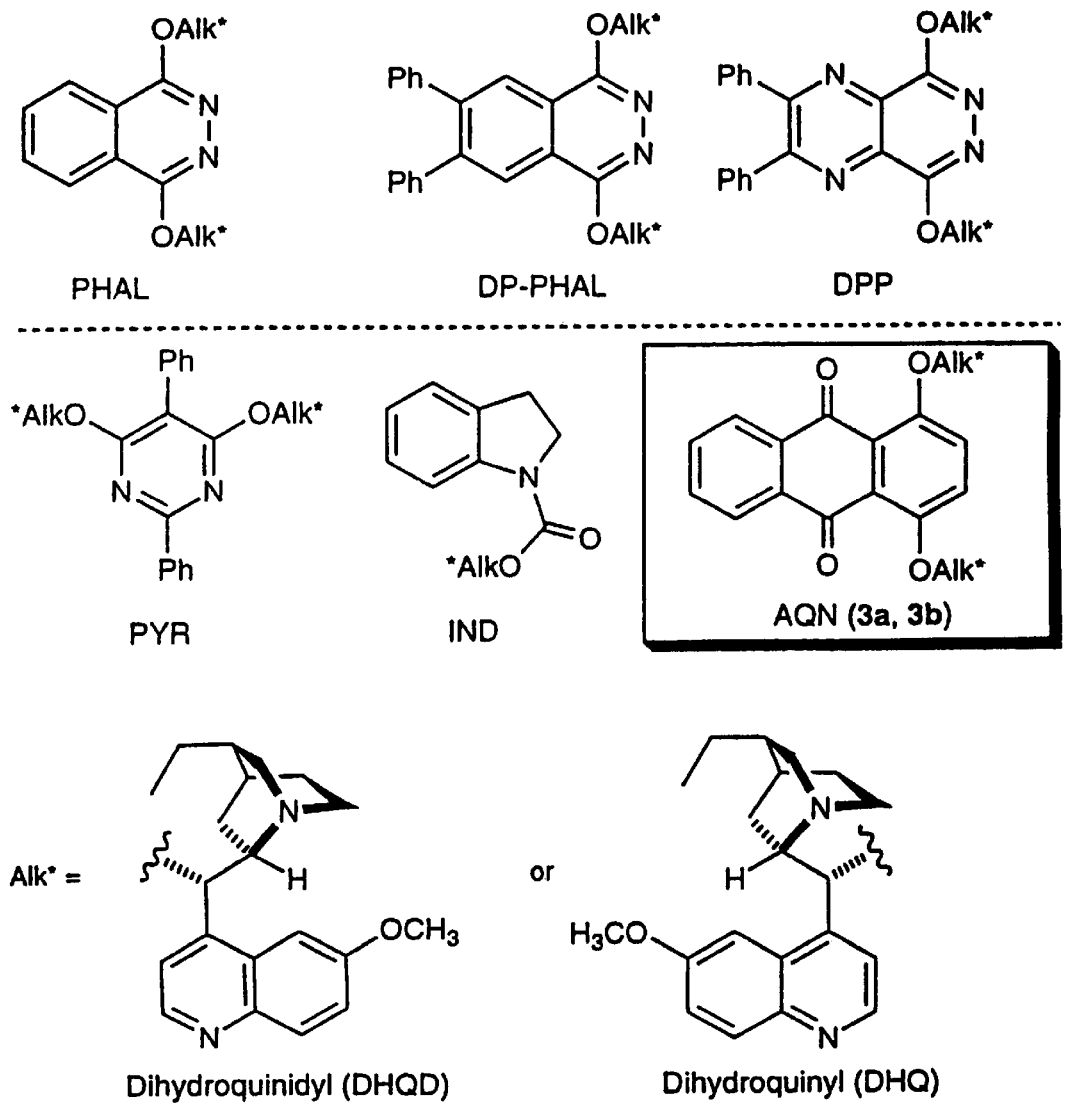
FIG. 9 illustrates the preferred ligand classes for aminohydroxylation wherein PHAL=Phalazine; DP-PHAL=diphenyl-phthalazine; DPP=diphenyl pyrazinopyridazine; PYR=pyrimidine; IND=indoline; AQN=anthraquinone; dihydroquinidyl (DHQD) and dihydroquinyl (DHQ).
Figure 10:
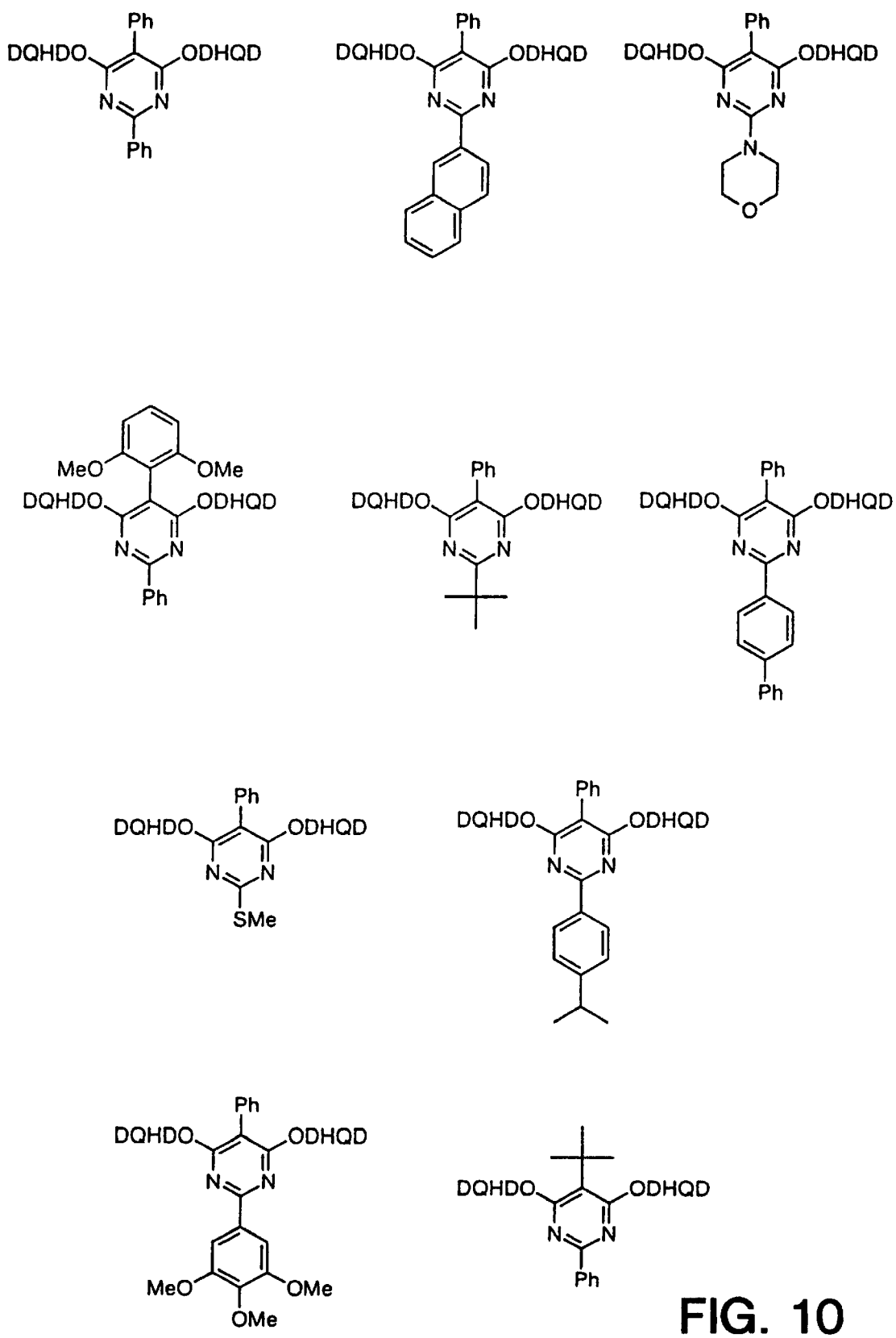
FIG. 10 illustrates additional ligands compatible for the asymmetric aminohydroxylation reaction.

FIG. 1 reveals the outcome for eight variously substituted cinnamate. All products were characterized by means of NMR, MS, melting point, optical rotation, and HPLC. All the results are good, even for the 2,6-disubstituted case in entry 7. While the "serine-regioselection" is lower (B:A≈4:1) than in the "isoserine-regioselection" (A:B≈7:1) with the PHAL-ligands, it is still very useful, especially since high asymmetric induction is observed (>90% ee) and with one exception (entry 7), the minor regioisomer A was easily removed by chromatography on silica gel. Due to the high overall yield of the AA regioisomers in all cases, the serine type products were isolated in yields up to 68% (entry 2).

Electron poor cinnamates proved less suitable with the AQN ligand system. For example, the AA of methyl 3-nitrocinnamate gave a 1:1 mixture of regioisomers and significant amounts of the diol by-product. On the other hand, changing the aromatic substituent for an aliphatic one, led to only a slight drop in the regioselectivity. Thus, methyl trans-2-octenoate afforded a 75:25 mixture favoring the 3-n-pentylserine regioisomer [using (DHQD)2AQN gave (2S,3R)-B, with n-pentyl in place of the aryl, in 93% ee].

In a typical experiment, a reaction flask immersed in a water bath was charged with sodium hydroxide (3.05 mmol of a commercial 1.022 N solution) and diluted with water (4.5 mL) in a dark fume hood. Part of this alkaline solution (c. 0.5 mL)4b was transferred into a vial to dissolve $K_2[OsO_2(OH)_4]$ (14.7 mg, 0.04 mmol). With vigorous stirring, n-propanol (4 mL) and benzyl carbamate (0.469 g, 3.1 mmol) were added to the flask, followed by dropwise addition of freshly prepared t-butyl hypochlorite (0.331 g, 0.346 mL, 3.05 mmol). After five minutes, an n-propanol solution (3.5 mL) of $(DHQD)_2AQN$ (34.3 mg, 0.04 mmol) (Aldrich cat. no.: 45,671–3) and methyl cinnamate (0.162 g, 1 mmol), and the aqueous $K_2[OsO_2(OH)_4]$ solution were added. After 1.5 h, the solution was quenched with 0.5 g sodium bisulfite. After the usual workup (Li, G.; Angert, H. H.; Sharpless, K. B. *Angew. Chem. Int. Ed. Engl.* 1996, 35, 2813–2817), 0.206 g (62% yield, 92% ee) of the pure (2S,3R)-N-benzyloxycarbonyl-3-phenylserine methyl ester (B, entry 1, R=H) was isolated via chromatography on silica gel (hexane/EtOAc=5:1, A elutes before B).

The reason for the difference between PHAL and AQN ligand classes for the AA of cinnamates is unknown and was unexpected. However, the substrate orientation within the binding pockets of these two different ligand classes is obviously altered in such a way that opposite regioselection results, but remarkably, without affecting the sense or the degree of the enantiofacial selectivity. Mechanistic understanding aside, the AA now provides a simple method to functionalize cinnamates and other olefins through direct introduction of an N,O-vicinal set of heteroatoms in a single step. These cis-additions are stereospecific, proceed with high asymmetric induction, and now also allow selective access to either of the aminoacid regioisomers.

II. Olefin Classes

The asymmetric aminohydroxylation (AA) works well with three olefin classes: 1) monosubstituted i (table 1); 2) cis-disubstituted iii (table 1), and 3) trans-disubstituted iv olefins. The 1,1 disubstituted ii and trisubstituted types of olefins give only racemic or low ee's while the tetrasubstituted class, vi, does not provide any signs of turnover.

TABLE I

| olefin class | i | ii | iii | iv | v | vi |
|---|---|---|---|---|---|---|
| AD ee range | good 30–99% | good 70–99% | poor 20–80% | excellent 90–>99.8% | excellent 90–99% | variable 20–97% |
| AA ee range | good Ar, 80–99% R, 40–80% | ? | good | excellent up to 99% | ? | ? |

III. Regioselectivity

High regioselectivity is one of the more useful features of the AA. The carbamate-version exhibits a strong preference for nitrogen attachment to the olefinic carbon bearing an aromatic substituent or, in the case of olefins conjugated with a strong electron withdrawing group (EWG), the nitrogen is strongly directed to the olefinic carbon distal to the EWG. Reversed regioselectivity is observed when AQN ligands are employed as illustrated in FIG. 1, parts A and B.

In particular, the AQN alkaloid ligand is responsible for high reversed regioselectivity with electron rich cinnamate based olefins as shown in the table of FIG. 1, part B. Product 1 is favored when the AQN ligand is employed. Alternatively, product 2 is favored when the PHAL ligand is employed (FIG. 1). When the ligand is omitted, there is little preference for either regioisomer. Beyond probable contributions from "binding pocket" effects, the strong regioselection phenomenon requires the operation of powerful electronic determinants.

IV. Mechanistic hypothesis (1) The Os=N—X linkage should be more polarized (especially when X is electron withdrawing) and also more reactive than the Os=O linkage. The Os=N—X linkage, therefore, reacts preferentially with the olefin to give osmaazetidine intermediates wherein the olefin osmium complexes have been omitted for clarity (Scheme II).

(2) Unsymmetric olefins such as cinnamate should strongly bias the insertion process favoring osmaazetidine 1i over its regioisomer 2i. Yet in the absence of a ligand roughly equal amounts of the regioisomeric products 1p and 2p (derived from 1i and 2i, respectively) are produced. This is not surprising since one might predict that the much weaker Os-C bond in 2i (c.f. same bond in 1i) could easily siphon much of the reaction through intermediate 2i (i.e. 2i to 2p) even if the concentration of 1i were a 1000 times greater (Scheme I).

Scheme I.

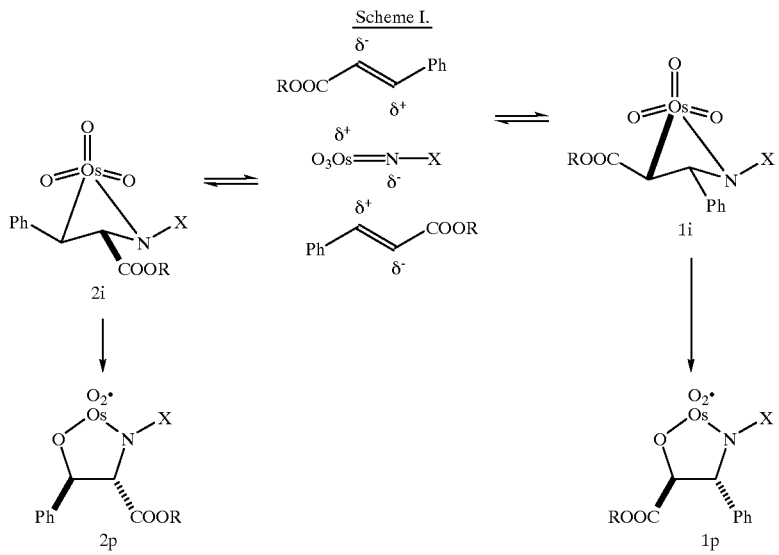

(3) Intervention by the chiral ligand can dramatically change the outcome (Scheme II). The "binding pocket" effect favors formation of ligated intermediate 1i'. In addition, rearrangement of the strong Os-C bond in 1i' (c.f. EWG effect on M-C bond strengths) to product 1p' is facilitated by both steric and orbital-electronic effects mediated by the ligand. In this way the factors which had destroyed regioselectivity in the absence of the ligand are overridden, and the reaction is channeled along a single path at each point of decision: (1) 3-aza or 2-aza product; and (2) S,R- or R,S-enantiomer. Here the ligand controls both the regio-and the enantioselectivity.

Scheme II.

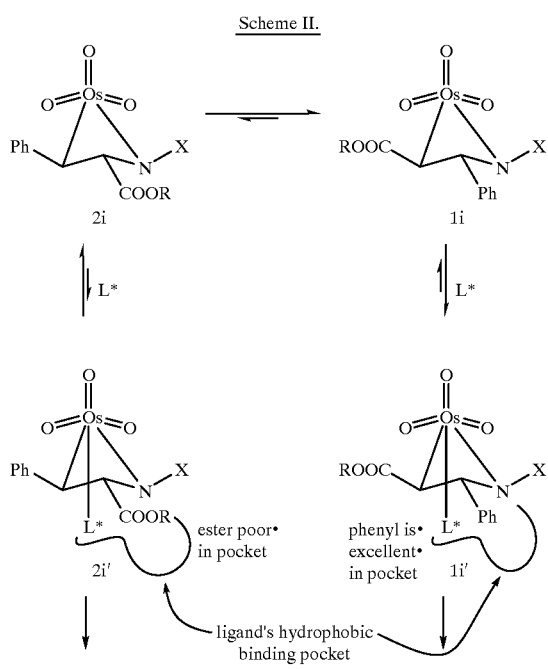

-continued

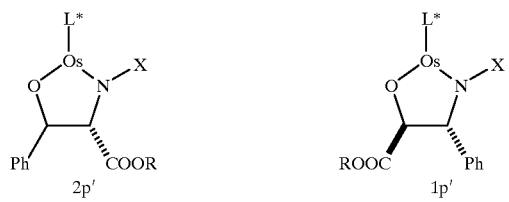

V Rationale for Olefin Preferences

A quadrant mnemonic for the key ligated osmaazetdine intermediate 1i' (scheme III) provides an explanation as to why only 3 of the 6 olefin classes appear to make good AA substrates. Three of the four quadrants are fairly easy to assign and to fit to the 3D-picture of the ligated osmaazetidine intermediate (Scheme III): (1) the NE quadrant can handle a large group, it corresponds to the pseudoequatorial substituent ($R_M$) on the carbon bound to osmium; (2) the SE quadrant is the one that presents as most crowded, supposedly due to the pseudoaxial substituent on the carbon bond to osmium which is very close to the ligand at its point of ligation to osmium (unless it is a hydrogen atom, things rarely go well in the AD or the AA); (3) the SW quadrant, as in the AD, gives every sign of possessing a good "binding pocket" for aryl and some alkyl substituents ($R_L$).

As before, the situation in the NW quadrant is less predictable. This quadrant encompasses the pseudoaxial substituent ($R_S$) bound to oxygen (AD) or nitrogen (AA) which in either case is close to the oxo group on osmium which is trans to the ligating nitrogen of the ligand. Hydrogen bonding groups in this position often have a positive effect on both the rates and the enantioselectivities of the asymmetric dihydroxylation (AD(reaction (Sharpless et al *Chem Rev.*, 1994, 2488).

Scheme III
AA mnemonic and 1i′-simple core (calculated)

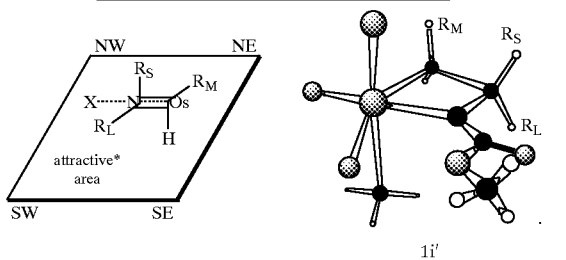

VI. Rationale for incompatiblilty with some olefin classes

A difference between the AA and the AD, which has important practical implications, is the loss of two major olefin classes for the AA. (The tetrasubstituted class vi, is ignored here since it is the least available class of olefins and has not been shown to work with the AA process). These are the 1,1-di- and trisubstituted classes (ii and v in the Table) which are generally very good in the AD. (Recall that so far the PHAL ligands have been used almost exclusively in our AA studies so these comparisons seem merited). Most attempted AA's on 1,1-di- and trisubstituted olefins have failed to give enantiomerically enriched products, although excellent yields of racemic aminohydroxylation products have occasionally resulted.

AA addition reactions with these substitution patterns have an explanation. In both cases a hydrogen substituent can be placed in the crucial SE quadrant. The stand-out difference between the AA and AD suggests a possible answer. The AA bears an extra substituent, the one on nitrogen, and most importantly, in the key intermediates this substituent is forced to be "in close," a consequence of the great reactivity of the Os=N-group to which it is attached. In our usual quadrant analysis this "new" substituent must find a place for itself in a region which is crowded by parts of the ligand and by substituents (originating from the olefin) on the osmaazetidine.

In the ligated osmaazetidine intermediate (Scheme IV) this nitrogen substituent lies roughly due West at the boundary of the NW and SW quadrants. In spite of negotiable open space in the "up/down direction" the nitrogen substituent could perturb the entire system, especially for olefins with substituents in both the NW and SW sectors. Any perturbing effects of the imido nitrogen substituent should diminish as it becomes smaller, and this prediction is dramatically born out by the results using smaller sulfonamides (e.g. $CH_3SO_2NH_2$) and the carbamates, which are inherently much smaller than any sulfonamide near the crucial point of attachment to nitrogen.

A reason that the AA process is poor for 1,1-di- and trisubstituted olefins is due to the fact that the Os=N-group reacts first forcing the ligand to bind to the osmaazetidine, which has a hydrogen in the SW quadrant. The relevant intermediates are A and B respectively:

A

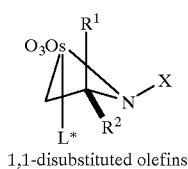

1,1-disubstituted olefins and

B

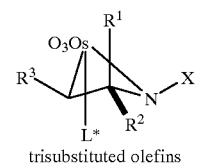

trisubstituted olefins

In either case, the nitrogen is forced to end up attached to a disubstituted carbon. The substituent on the nitrogen may destabilize the resulting ligated osmaazetidine intermediates A and B in a manner which does not occur for the analogous ligated osmaoxetanes.

While olefin classes ii and v may never enter the useful range in these AA processes, one can imagine using the electronic and binding pocket effects to create "ideal" substrates even for difficult classes, e.g.

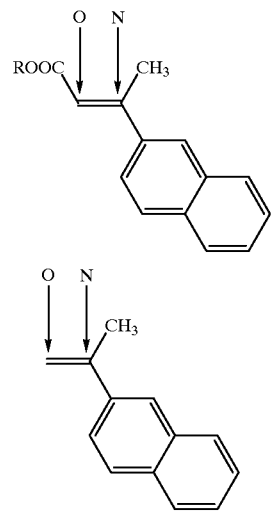

In light of the above speculations, one might wonder why the cis-disubstituted olefins (iii) represent a successful class in the AA. These olefins are also forced to have a substituent in the NW quadrant. However, now there is only one substituent on the carbon bound to nitrogen in the key intermediate related to B (i.e. $R_2$=H). This will increase the conformational flexibility of the intermediate making cis-disubstituted olefins good candidates for the AA process.

Cleavage to Produce Aryl Serine:

Cleavages of the hydroxycarbamates, to free aminoalcohols, can employ mild acid or base hydrolysis and catalytic hydrogenolysis, depending on the attached functionality to the carbamate. (Greene, *Protective Groups in Organic Synthesis*, 1981, Wiley, 1st edn. pp. 223–249).

Synthetic Protocals

NMR spectra were recorded on Bruker AMX-500, AM-300, or AM-250 instruments. The following abbreviations were used to explain the multiplicities: s, singlet; d, doublet; t, triplet; q, quartet; m, multiplet; apt, apparent; b, broad; obs, obscured. IR spectra were recorded on Nicolet 205, Perkin Elmer 1600 or Galaxy 2020 series FT-IR spectrophotometers. Optical rotations were recorded using a Perkin Elmer 241 polarimeter. High-resolution mass spectra (HRMS) were recorded on a VG ZAB-ZSE mass spectrometer under Fast Atom Bombardment (FAB) conditions, at the Scripps Research Institute.

All reactions were monitored by color change, HPLC, GC or thin-layer chromatography carried out on 0.25 mm Whatman silica gel plates (K6F-60 Å) using UV light, p-anisaldehyde, or 7% ethanolic phosphomolybdic acid and heat as developing agent. E. Merck silica gel (60, particle size 0.040–0.063 mm) was used for flash column chromatography. Tetrahydrofuran (THF) and ethyl ether were distilled from sodium-benzophenone and methylene chloride, benzene and toluene were distilled from calcium hydride. All reagents were obtained from Aldrich Chemical Co. Inc. unless otherwise noted. Solvents used for workup, chromatography, and recrystallizations were reagent grade from Fisher Scientific and were used as received.

Example of Reversal of Regioselection Standard Conditions: synthesis of (2S,3R)-N-benzyloxycarbonyl-3-phenylserine methyl ester (B, entry 1, R=H) as in FIG. 1:

To a reaction flask immersed in a water bath was charged with sodium hydroxide (3.05 mmol of a commercial 1.022 N solution) and diluted with water (4.5 mL) in a dark fume hood. Part of this alkaline solution (c. 0.5 mL)4b was transferred into a vial to dissolve $K_2[OsO_2(OH)_4]$ (14.7 mg, 0.04 mmol). With vigorous stirring, n-propanol (4 mL) and benzyl carbamate (0.469 g, 3.1 mmol) were added to the flask, followed by dropwise addition of freshly prepared t-butyl hypochlorite (0.331 g, 0.346 mL, 3.05 mmol). After five minutes, an n-propanol solution (3.5 mL) of $(DHQD)_2AQN$ (34.3 mg, 0.04 mmol) (Aldrich cat. no.: 45,671–3) and methyl cinnamate (0.162 g, 1 mmol), and the aqueous $K_2[OsO_2(OH)_4]$ solution were added. After 1.5 h, the solution was quenched with 0.5 g sodium bisulfite. After the usual workup (Li, G.; Angert, H. H.; Sharpless, K. B. *Angew. Chem. Tnt. Ed. Engl.* 1996, 35, 2813–2817), 0.206 g (62% yield, 92% ee) of the pure (2S,3R)-N-benzyloxycarbonyl-3-phenylserine methyl ester (B, entry 1, R=H) was isolated via chromatography on silica gel (hexane/EtOAc=5:1, A elutes before B).(2S,3R)-B, R=H: M.p. 107–108° C.; $[\alpha]_D^{25}$=−26.9 (c=1 in 95% EtOH); $^1$H-NMR (400 MHz, $CDCl_3$): d=7.35–7.23 (m, 10 H), 5.55 (d, J=8.5 Hz, 1H), 5.38 (s, 1H), 4.99 (s, 2H), 4.59 (dd, J=2.5, 9.1 Hz, 1H), 3.75 (s, 3H), 2.56 (br s, 1H); $^{13}$C-NMR (150 MHz, $CDCl_3$) : d=171.1, 158.9, 139.5, 136.1, 128.5, 128.2, 128.1, 127.9, 126.2, 125.9, 73.7, 67.0, 59.7, 52.7; HRMS calcd. for $C_{18}H_{19}NO_5$ $(M+Na)^+$: 352.1161, found: 352.1152; HPLC: Chiralcel OD-H, 0.46 cm×25 cm, hexane/i-PrOH 85/15, 0.6 mL/min, 210 nm, 30.1 min (2R,3S), 33.7 min (2S, 3R). The absolute configuration of this compound was determined by hydrogenolytic removal of the CBz-group, followed by comparison of the resulting aminohydroxyester's optical rotation with the literature value; Beulshausen et al. *Liebigs Ann. Chem.* 1991, 1207–1209.

Chloramine Sodium Salt Preparation

Procedure as adapted from Campbell et al. *Chem. Rev.*, 1978, 78, 65.

General Asymmetric Aminohydroxylation Conditions Using PHAL Ligands:

To a solution of NaOH (3.05 equivalents) in 0.13 Molar equivalent of water to olefin is added desired carbamate (3.10 equivalents). The resulting solution is stirred at room temperature for 10 min and then t-butyl hypochlorite (3.05 equivalents; Aldrich Chemical) is added dropwise. The above solution is stirred for another 10 min and then 0.13 Molar equivalent of n-propanol (t-butanol or acetonitrile can be substituted) and $(DHQ)_2$-PHAL (0.05 equivalents, 5 mol %; DHQD 2-PHAL obtains antipode) are added to form a homogeneous solution. The reaction mixture is immersed in a room temperature bath and added substrate olefin (1 equivalents) and $K_2OsO_2(OH)_4$ (0.04 equivalents, 4 mol %) are then added. The reaction is stirred for 45 min with the color changing from light green to light yellow, followed by quenching by addition of aqueous sodium sulfite; the phases are separated, and the aqueous phase was extracted with ethyl acetate. The combined organic extracts are washed with water and brine, dried over $MgSO_4$ and the solvent concentrated to give the crude product. Flash chromatography of this material provides the hydroxycarbamate product.

General Reversed Asymmetric Aminohydroxylation Conditions Using AQN Ligands:

To a solution of NaOH (3.05 equivalents) in 0.13 Molar equivalent of water to olefin is added desired carbamate (3.10 equivalents). The resulting solution is stirred at room temperature for 10 min and then t-butyl hypochlorite (3.05 equivalents; Aldrich Chemical) is added dropwise. The above solution is stirred for another 10 min and then 0.13 Molar equivalent of n-propanol (t-butanol or acetonitrile can be substituted) and $(DHQ)_2$-AQN (0.05 equivalents, 5 mol %; $DHQD_2$-AQN obtains antipode) are added to form a homogeneous solution. The reaction mixture is immersed in a room temperature bath and added substrate olefin (1 equivalents) and $K_2OsO_2(OH)_4$ (0.04 equivalents, 4 mol %) are then added. The reaction is stirred for 45 min with the color changing from light green to light yellow, followed by quenching by addition of aqueous sodium sulfite; the phases are separated, and the aqueous phase was extracted with ethyl acetate. The combined organic extracts are washed with water and brine, dried over $MgSO_4$ and the solvent concentrated to give the crude product. Flash chromatography of this material provides the hydroxycarbamate product.

Solvent Variations:

Preferred solvents include acetonitrile, n-propanol, tert-butanol.

Suitable solvents include methanol, ethanol, n-butanol, n-pentanol, 2-Propanol, 2-Butanol, tert-butanol, ethylene glycol; nitriles: acetonitrile, propionitrile; ethers: tetrahydrofurane, diethyl ether, tert. butyl methyl ether, dimethoxyethane, 1,4-dioxane; miscellaneous: dimethyl formamide, acetone, benzene, toluene, chloroform, methylene chloride.

Percent Water/Organic Solvent Variations

Figure 11:
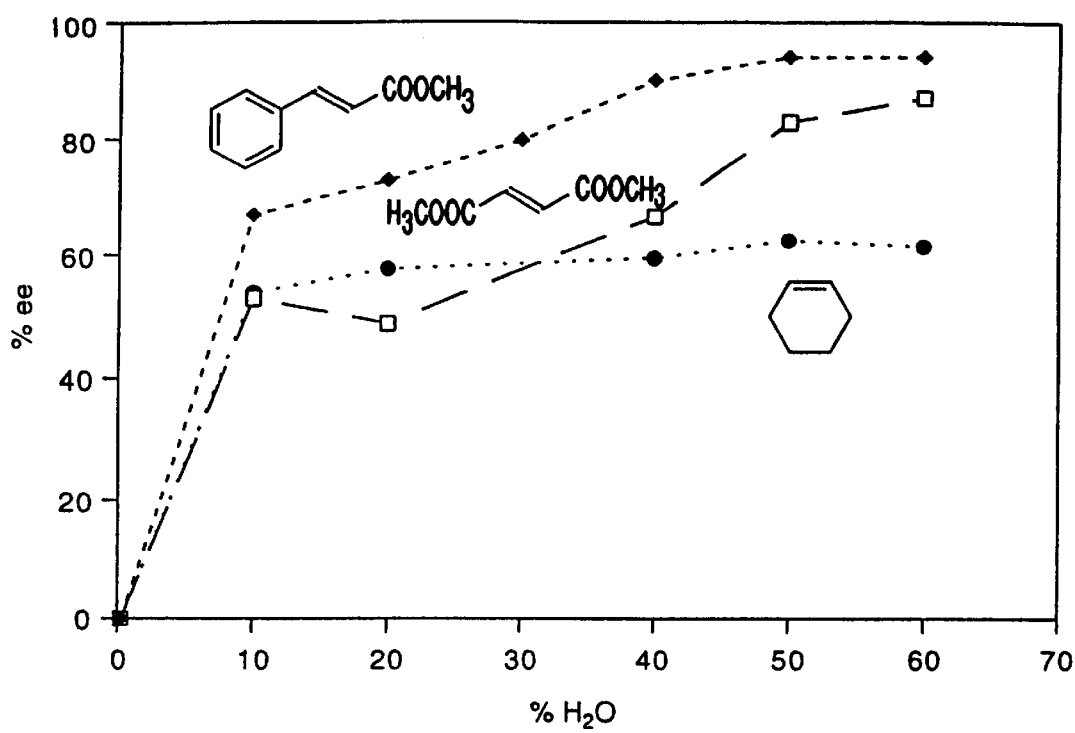
FIG. 11 illustrates the effects of water on the enantioselectivity of the asymmetric aminohydroxylation. The horizontal axis shows % water in increasing organic solvent (right side of graph; solvent used was n-propanol but acetonitrile, tert-butanol can also be used) where 0% water (left side of graph) indicates 100% organic solvent. The vertical axis shows % ee (enantioselectivity). Three substrates are shown including methyl cinnamate (dark diamond—medium dashed line), dimethylfumarate (open box—long dashed line) and cyclohexene (dark circle—short dashed line). No turnover and therefore no enantioselectivity is found at 0% water. Optimal concentration for highest enantioselectivity is approximately 50% water/50% organic solvent but can vary between 10–60% depending on substrate.
Figure 12:
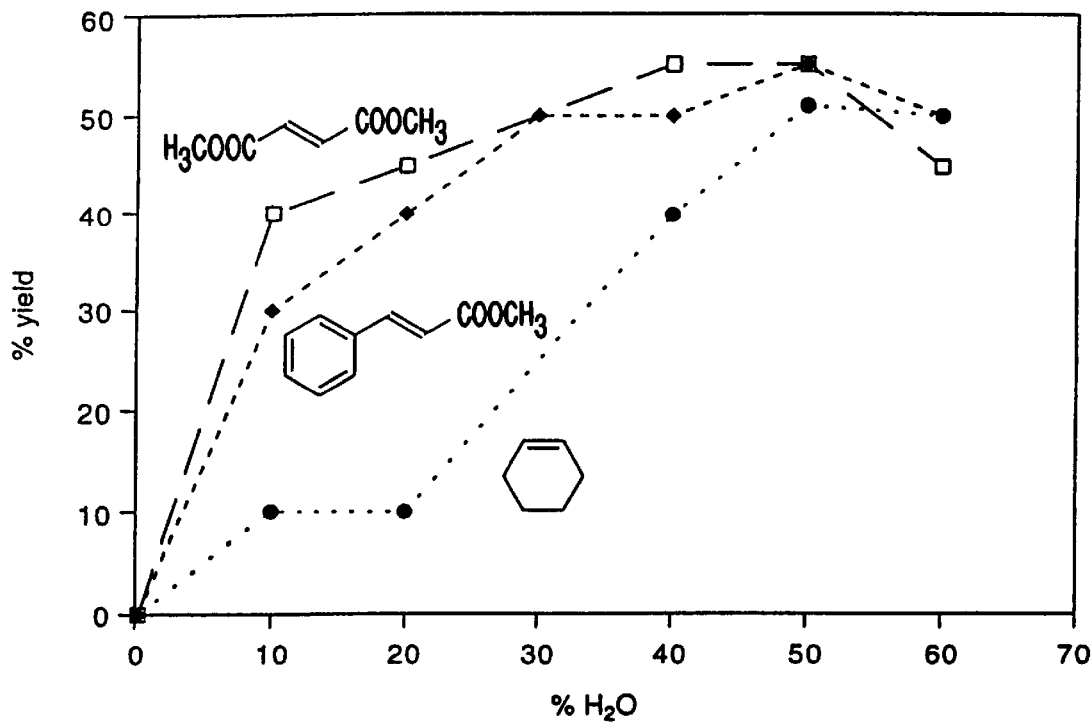
FIG. 12 illustrates the effects of water on the yields of the asymmetric aminohydroxylation. The horizontal axis shows % water in increasing organic solvent (right side of graph; solvent used was n-propanol but acetonitrile, tert-butanol can also be used) where 0% water (left side of graph) indicates 100% organic solvent. The vertical axis shows % yield. Three representative substrates are shown including methyl cinnamate (dark diamond—medium dashed line), dimethylfumarate (open box—long dashed line) and cyclohexene (dark circle—short dashed line). No turnover is found at 0% water. Optimal concentration for highest yield is approximately 50% water/50% organic solvent but can vary between 10–60% depending on substrate.
Figure 13:
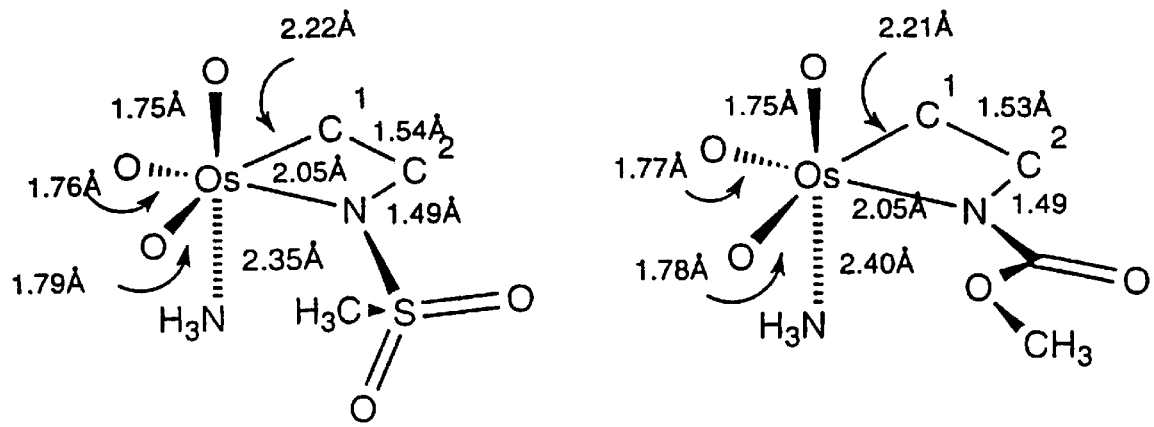
FIG. 13 illustrates a molecular modeling study which was performed on both carbamate and sulfonamide osmium complexes; key intermediates in the catalytic process. The structures of N-methylsulfonyl- and N-methoxycarbonyl osmaazetidines were optimized by density functional theory (DFT) with Becke's three parameter hybrid method using LYP correlation functional (B3LYP). The calculations were performed by using Gaussian 94 program[1] with LanL2DZ basis set. Due to the complexity of the chiral ligands, a simplied model was used. Models of N-methylsulfonyl-and N-methoxycarbonyl-osmaazetidines were adopted where the osmium atom was complexed with ammonia instead of the chiral ligand. The calculations show that the osmaazetidine rings have the flat conformations with no significant puckering as observed in osmaoxetanes. The osmaazetidine nitrogen is slightly pyramidised in the methylsulfonyl case. In the carbamate case, the osmaazetidine nitrogen is planar. The osmaazetidines are possible intermediates in [2+2] mechanistic pathway of the AA. Dihedral and bond angles are indicated.
Figure 14:
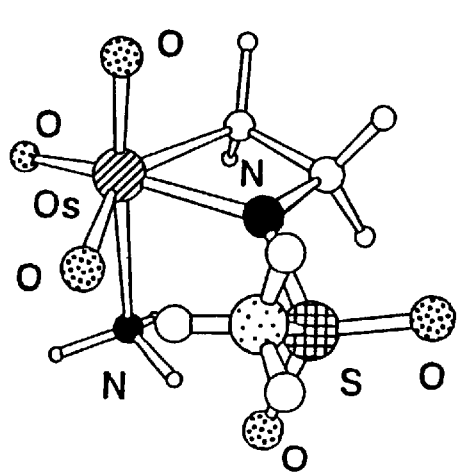
FIG. 14 illustrates a ball and stick view of the molecular modeling study as shown in FIG. 13 and performed on both carbamate and sulfonamide osmium complexes.
Figure 14:
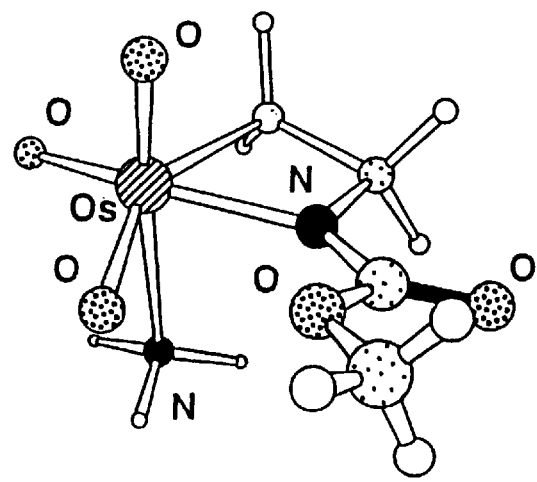
Figure 15:
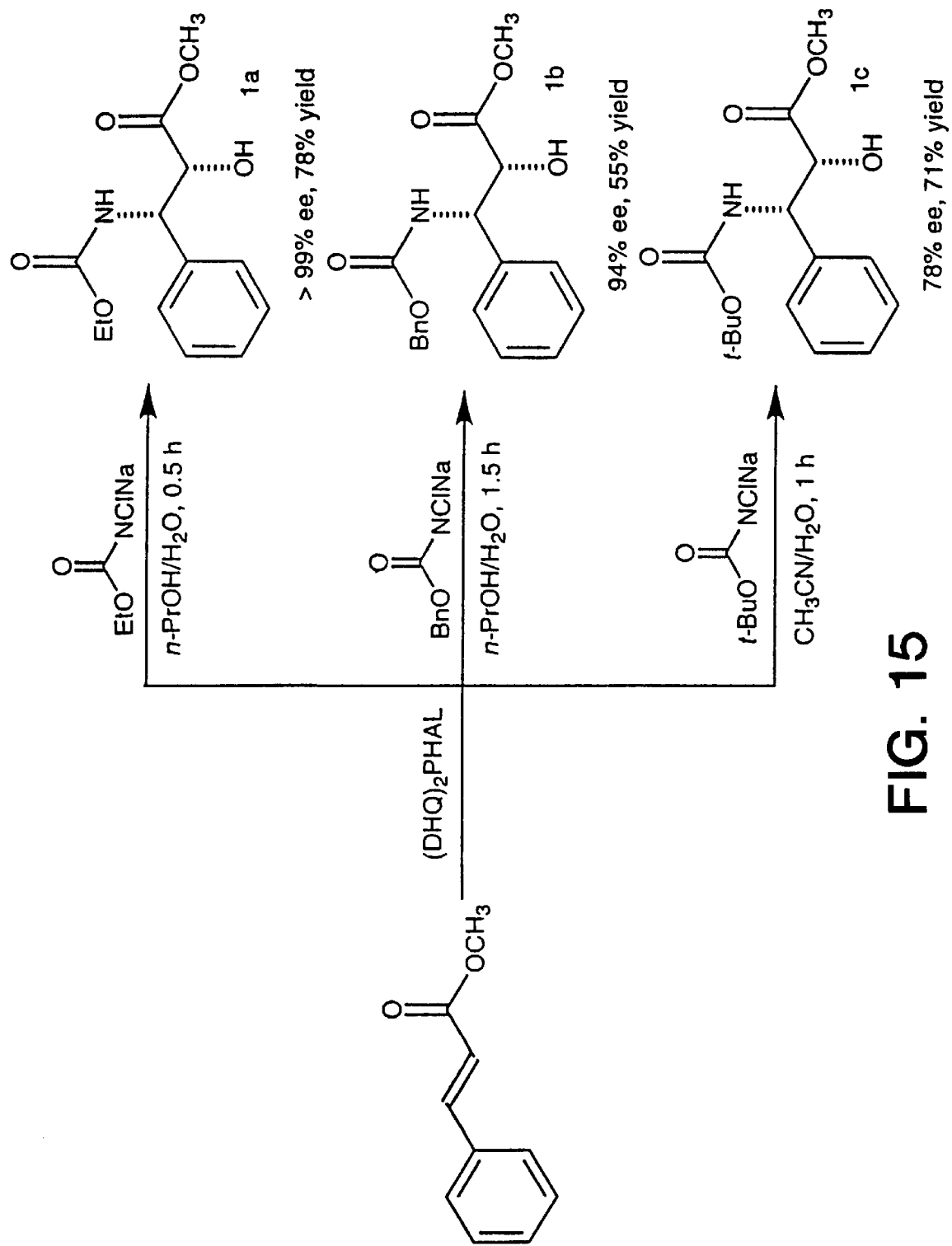
FIG. 15 illustrates a variety of sodio-N-chloro-carbamate oxidants for the asymmetric aa reaction.

Two key points are that the ee and especially the yields are lower in the low water range (see FIGS. 11 and 12). No reaction is seen with only 2 to 4 equiv of water present which must be much less than 0.1% water These same "minuscule" amounts of water" conditions work great for the silver and mercury salts of the N-chlorocarbamates in the old catalytic aminohydroylation process with no chiral ligands present.

Solvent Concentration Variations,

In its present form the process starts to give lower selectivities for some substrates when the concentration of olefin (which of course prescribes the standard concentration of all the other species) gets much above 0.1 molar.

Ligand Variations:

For reversed conditions, the AQN ligand can range from ca. 1 to 10 mol % (less is appropriate for lower temperatures; eg. 1% might be enough at 0° C. and 10% would probably be needed to keep the % ee at reasonable levels if the temperature reaches 35 or 40° C. In practice, the molarity of the ligand matters and the amount of ligand needed to realize the "ceiling ee" scales directly with the reaction concentration (ie if twice the volume of solvent is used, then the mol % of ligand added must also double to keep its molarity constant and correspondingly if the reaction is run twice as concentrated as usual (see general recipe below) then half of the usual mol % ligand gives the needed ligand molarity). Because the crucial binding of the ligand is an extremely rapid bimolecular process, the equilibrium constant is highly sensitive to temperature which is why the molarity of ligand needed, increases rapidly with temperature.

Osmium Variations:

The amount of Os catalyst can range from 0.5% (probably even less in the very best cases, and in any case the number will drop as the process if further improved) to 10 or even 20%. The general procedure conditions uses 4% to have fast reaction times, but 2% is good for most cases. The high loadings of 20%, for example, is needed to achieve reasonable rates with very poor substrates (this conclusion follows from the extensive experience by us and others with the AD, where in desparate situations 20 or more % Os catalyst is needed.

Temperature Variations:

For most cases, the carbamate AA process is run between 10 and 25 degrees C. There may be cases where 0 degrees—up to 35 to 40 degrees may be advantageous depending on substrate.

Deprotection Conditions of Carbamate to Free Amine t-BOC: TFA procedure: Lundt et al *Int. J. Pept. Protein Res.*, 1978, 12, 258; HCl procedure: Stahl et al. *J. Org. Chem.*, 1978, 43, 2285.

Benzyl carbamate: Hydrogenation procedure: Bergman et al *Ber.*, 1932, 65, 1192.

Ethyl and methyl carbamate: Trimethylsilyliodide procedure: Lott et al. *J. Chem. Soc. Chem. Comm* 1979, 495; HBr procedure: Wani et al *J. Am. Chem. Soc.*, 1972 94, 3631.

Transformation of R—COOH to R—COOMe

Procedure as adapted from Chan et al. *Synthesis* 1983, 201.

What is claimed:

1. A method for synthesizing an aryl serine comprising the following steps:

Step A: converting a cinnamate based olefinic substrate to an asymmetric β-hydroxycarbamate product by asymmetric addition of a carbamoyl radical and a hydroxyl radical to the olefinic substrate, the method being of a type which employs a reaction solution which includes a carbamate as a source of the carbamoyl radical, osmium as a catalyst, an anthraquinone based chiral ligand for regioselectively and enantiomerically directing said asymmetric addition, and a solvent having an organic component, the cinnamate based olefinic substrate and carbamate being present and soluble in stoichiometric amounts within the solvent, the osmium being present and soluble in catalytic amounts within the solvent, the anthroquinone (AQN) based chiral ligand being present and soluble within the solvent; and then Step B: cleaving the asymmetric β-hydroxycarbamate product of said Step A to produce the aryl serine.

2. The method for converting a cinnamate based olefinic substrate to an asymmetric β-hydroxycarbamate product as described in claim 1, wherein, in said Step A, the anthraquinone based chiral ligand is selected from a group consisting of (dihyrodquininyl)$_2$-AQN and (dihyrodquindinyl)$_2$-AQN.

3. The method for converting a cinnamate based olefinic substrate to an asymmetric β-hydroxycarbamate product as described in claim 2, wherein:

the organic component of the solvent is selected from the group consisting of acetonitrile, tert-butanol, ethanol, and n-propanol.

4. The method for converting a cinnamate based olefinic substrate to an asymmetric β-hydroxycarbamate product as described in claim 3, wherein:

in said Step A, the aqueous and organic components of the solvent are each approximately 50% on a volume basis.

* * * * *